United States Patent
Prais (10) Patent No.: US 12,076,536 B2
(45) Date of Patent: Sep. 3, 2024

(54) SYRINGE PLUNGER STOPPER FOR HIGH DOSE ACCURACY DRUG DELIVERY

(71) Applicant: Becton, Dickinson and Company, Franklin Lakes, NJ (US)

(72) Inventor: Alfred W. Prais, Hewitt, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 436 days.

(21) Appl. No.: 16/957,971

(22) PCT Filed: May 14, 2019

(86) PCT No.: PCT/US2019/032164
§ 371 (c)(1),
(2) Date: Jun. 25, 2020

(87) PCT Pub. No.: WO2019/222174
PCT Pub. Date: Nov. 21, 2019

(65) Prior Publication Data
US 2020/0330690 A1    Oct. 22, 2020

Related U.S. Application Data

(60) Provisional application No. 62/671,618, filed on May 15, 2018.

(51) Int. Cl.
*A61M 5/31* (2006.01)
*A61M 5/315* (2006.01)

(52) U.S. Cl.
CPC .... *A61M 5/31513* (2013.01); *A61M 5/31545* (2013.01); *A61M 2205/0216* (2013.01); *A61M 2207/00* (2013.01)

(58) Field of Classification Search
CPC .......... A61M 5/31511; A61M 5/31513; A61M 5/31515
See application file for complete search history.

(56) References Cited

U.S. PATENT DOCUMENTS 4,911,695 A * 3/1990 Lindner ............. A61M 5/31511
604/218
5,007,904 A    4/1991 Densmore et al.
(Continued)

FOREIGN PATENT DOCUMENTS

| CN | 103533977 A | 1/2014 |
| GB | 578827 | 7/1946 |

(Continued)

*Primary Examiner* — William R Carpenter
(74) *Attorney, Agent, or Firm* — The Webb Law Firm (57) ABSTRACT

A plunger stopper (12) configured for attachment with a plunger rod (14) for use with a within a syringe barrel for high dose accuracy drug delivery. The stopper having a first portion (40) formed from a first material and a second portion (42) formed from a second material, wherein the second material has a greater rigidity than the first material and wherein the second portion is configured to be attached to a plunger rod. The second material can be in the form of an insert (44) which functions to reduce the amount of distortion of the stopper during use, reduce air bubble size variation from fill to fill, maintain a seal with the inner wall of the syringe barrel with lower contact pressure in a resting state and reduce the amount of hysteresis of the stopper. The stopper can be adapted for use with infusers, pens, and other types of auto-injectors.

16 Claims, 13 Drawing Sheets

(56) References Cited

U.S. PATENT DOCUMENTS

| | | |
|---|---|---|
| 7,645,264 B2 | 1/2010 | Marsh et al. |
| 8,568,359 B2 | 10/2013 | Carrel et al. |
| 9,289,557 B2 | 3/2016 | Ivosevic et al. |
| 2006/0229562 A1 | 10/2006 | Marsh et al. |
| 2007/0060896 A1* | 3/2007 | Miller .............. A61M 5/31513 604/222 |
| 2007/0156102 A1 | 7/2007 | Py |
| 2009/0177159 A1 | 7/2009 | Knopper et al. |
| 2010/0268170 A1 | 10/2010 | Carrel et al. |
| 2012/0136298 A1* | 5/2012 | Bendix ............. A61M 5/31515 29/428 |
| 2017/0368264 A1* | 12/2017 | Fournier ........... A61M 5/31513 |

FOREIGN PATENT DOCUMENTS

| | | | |
|---|---|---|---|
| JP | 2002172168 A | 6/2002 | |
| JP | 2009534073 A | 9/2009 | |
| WO | 9530444 A1 | 11/1995 | |
| WO | 2007027585 A2 | 3/2007 | |
| WO | 2016120565 A1 | 8/2016 | |
| WO | 2017011599 A1 | 1/2017 | |
| WO | WO-2018152059 A1 * | 8/2018 | ........... A61B 5/0022 |

\* cited by examiner

SYRINGE PLUNGER STOPPER FOR HIGH DOSE ACCURACY DRUG DELIVERY

CROSS-REFERENCE TO RELATED APPLICATION

This application is the United States national phase of International Application No. PCT/US2019/032164 filed May 14, 2019, and claims priority to United States Provisional Application 62/671,618, entitled "Syringe Plunger Stopper for High Dose Accuracy Drug Delivery", and filed May 15, 2018, the disclosures of which are hereby incorporated by reference in their entirety.

BACKGROUND OF THE INVENTION

Field of the Invention

The invention relates, in general, to a stopper for high dose accuracy drug delivery, such as for use in syringes, infusers, pens, and other types of auto-injectors, and more particularly, to a stopper that has a reduced amount of distortion, a reduced air bubble size variation from fill to fill, and maintains a seal with the inner wall of the syringe barrel with lower contact pressure in a resting state. The stopper also has a reduced amount of hysteresis, i.e., the phenomenon in which the value of a physical property lags behind changes in the effect causing the change.

Efforts to improve dose accuracy with injection pens, auto-injectors, and other types of syringes have been attempted. These efforts have met with some success but often this success is offset by increased costs of the device, complexity of the devices, and/or unsustainable tolerances applied to the parts in the injector drive unit, such as setting of the dial ratchets, gear racks, and the like. Even after these efforts, dose variations still occurred due to stopper performance in the fluid path failing to meet certain compliance criteria. These failings typically occur due to distortion of the elastomeric vial closure (if so equipped) and the plunger stopper and their hysteresis, i.e., the lag in response exhibited by a body in reacting to changes in the forced affecting it, once the load is removed, as well as the remaining air bubble in the liquid after the stopper is placed.

Auto-injectors are typically used by non-medical personnel to self-inject themselves with certain medicines that require regular injections of drugs or products, i.e., on a daily basis. Because the person injecting themselves is typically not well educated on the operation of medical injection products, there is a need for self-injection devices that are simple to use and also very safe. In particular, the insertion of the needle must be performed at the right depth, the correct dose of product must be injected, and the injector must be deactivated after use before it is disposed of so that accidental needle stick injuries are avoided. The assembly and operation of a typical auto-injector is described in commonly-assigned U.S. Pat. No. 8,568,359, which is hereby incorporated by reference in its entirety.

Medication delivery pens are used for self-injection of precisely measured doses of medication. Medication delivery pens are widely used, i.e., by diabetics to self-inject insulin. A typical medication delivery pen includes a cartridge, which contains a volume of liquid medication sufficient for several doses. Using a pen needle, attached to the pen device, the dose is injected into a tissue area, such as the intramuscular tissue layer, the subcutaneous tissue layer, or the intradermal tissue layer. The assembly and operation of a typical pen injection device is described in commonly-assigned U.S. Pat. No. 7,645,264, which is hereby incorporated by reference in its entirety.

SUMMARY OF THE INVENTION

According to one aspect, the invention comprises a stopper adapted for attachment with a plunger rod for use within a syringe barrel for accurate dispensing of a fluid. The stopper comprises a first portion limited from a first material and a second portion formed from a second material, wherein the second material has a greater rigidity than the first material. The second portion is configured to be attached to the plunger rod. According to one embodiment, the second portion comprises an insert. The insert can be formed from a semi-rigid or rigid material. According to one example, the insert can be fabricated from metal, such as aluminum, zinc, extruded, stamped or cast steel, and the like. According to another example, the insert can be formed from a non-metallic material having rigid or semi-rigid properties, i.e., polyether ether ketone (PEEK), or epoxy resins, or similar but less expensive polyetherimide, having a glass transition temperature that is higher than the temperatures required for molding rubber.

The insert can be formed by an injection molding or by an extrusion/cutting process or by a sintering process. Internal threads can be located within the second portion for mating with the plunger rod. It can be appreciated that the insert can be secured to the plunger rod by other well-known techniques, such as friction fit and the like.

The first material can comprise an elastomeric material, such as those materials typically used for stoppers. The first material can be molded about the second material/insert. Alternatively, the insert can be embedded in the first material of the first portion. According to one design, the second portion or insert can comprise a tubular member having radially extending barbs about an outer surface thereof, configured for embedding the second portion or insert within the first material of the first portion. The insert can be a "C"-shaped member providing some flexibility to the insert. According to one embodiment, the tubular member/insert can have a closed front face for directly supporting the first material at a front face of the stopper.

According to another embodiment, the stopper can comprise a third portion forming a distal end of the stopper, the third portion formed from a third material comprising an elastomeric material having barrier properties. Alternatively, the distal end of the stopper can be coated with a barrier film such as ethylene tetrafluoroethylene (ETFE), or microporous membranes such as PTFE, expanded PTFE (ePTFE), polypropylene (PP) or polyethylene (PE), that minimize the drug product contact with the base rubber thereby blocking leeching of rubber components into the drug product.

According to another aspect, the invention comprises a stopper adapted for attachment with a plunger rod for use with an auto-injector for accurate dispensing of a fluid, the stopper comprising a first portion formed from a first material and a second portion formed from a second material, wherein the second material has a greater rigidity than the first material. The second portion is configured to be attached to the piston rod. The piston rod can be a spring-loaded piston rod. The first material of the first portion of the stopper comprises an elastomeric material and the second portion comprises an insert formed from a semi-rigid or rigid material. The insert can be embedded within the elastomeric material of the first portion.

According to yet another aspect, the invention comprises a stopper adapted for attachment with a lead screw for use with an injection medication delivery pen having a dosage knob for accurate dispensing of a fluid, the stopper comprising a first portion formed from a first material and a second portion formed from a second material, wherein the second material has a greater rigidity than the first material and wherein the second portion is configured to be attached to the lead screw. The dosage knob and lead screw are configured to set the dosage of the fluid to be injected and to inject the dosed fluid via the lead screw and the stopper from a medicament cartridge attached to a medication delivery pen. The first material of the first portion of the stopper comprises an elastomeric material and the second portion comprises an insert formed from a semi-rigid or rigid material. The insert can be embedded within the elastomeric material of the first portion.

BRIEF DESCRIPTION OF THE DRAWING

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Figure 1:
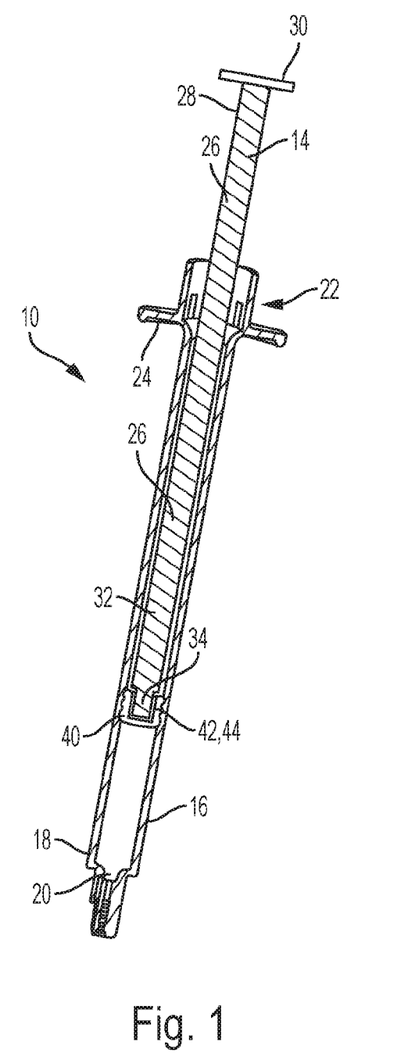
FIG. 1 is a cross-sectional view of a syringe assembly including a stopper for high dose accuracy drug delivery in accordance with an embodiment of the invention.
Figure 2:
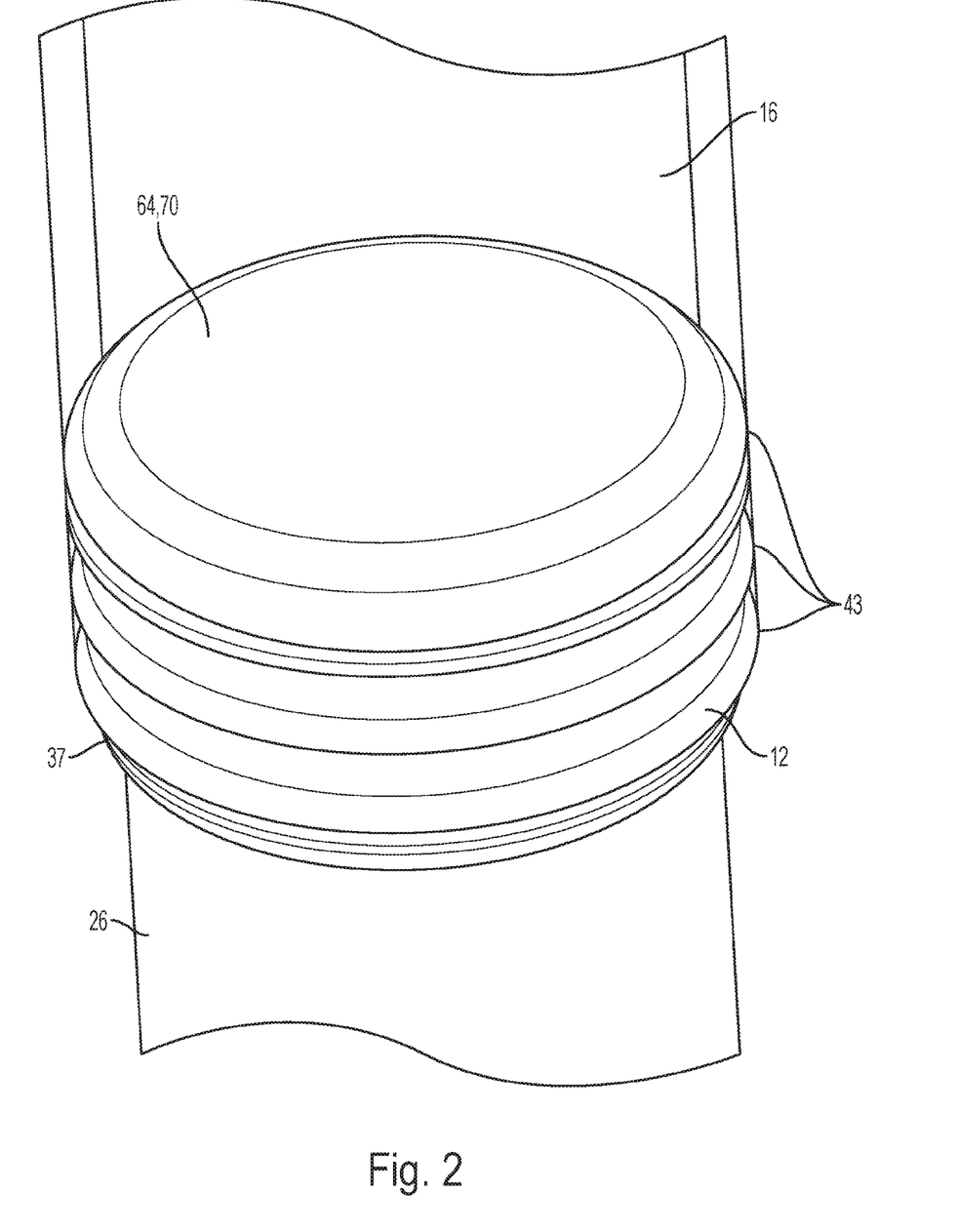
FIG. 2 is a top perspective view of the stopper of FIG. 1 in accordance with an embodiment of the invention.

Reference is now made to FIG. 1, which shows a cross-sectional view of a syringe assembly, generally indicated as 10, including a stopper 12 for high dose accuracy medication delivery. The syringe assembly includes a plunger rod 14. The stopper 12 and plunger rod 14 are adapted for use within a syringe barrel 16. The syringe barrel 16 has a generally elongate body including a distal or frontal end 18, which includes an outlet opening and/or a mechanism for attachment of a separate medical device, such as a leer 20, and an open proximal or rearward end 22 having finger grips 24 for receiving the stopper 12 and plunger rod 14.

Figure 3:
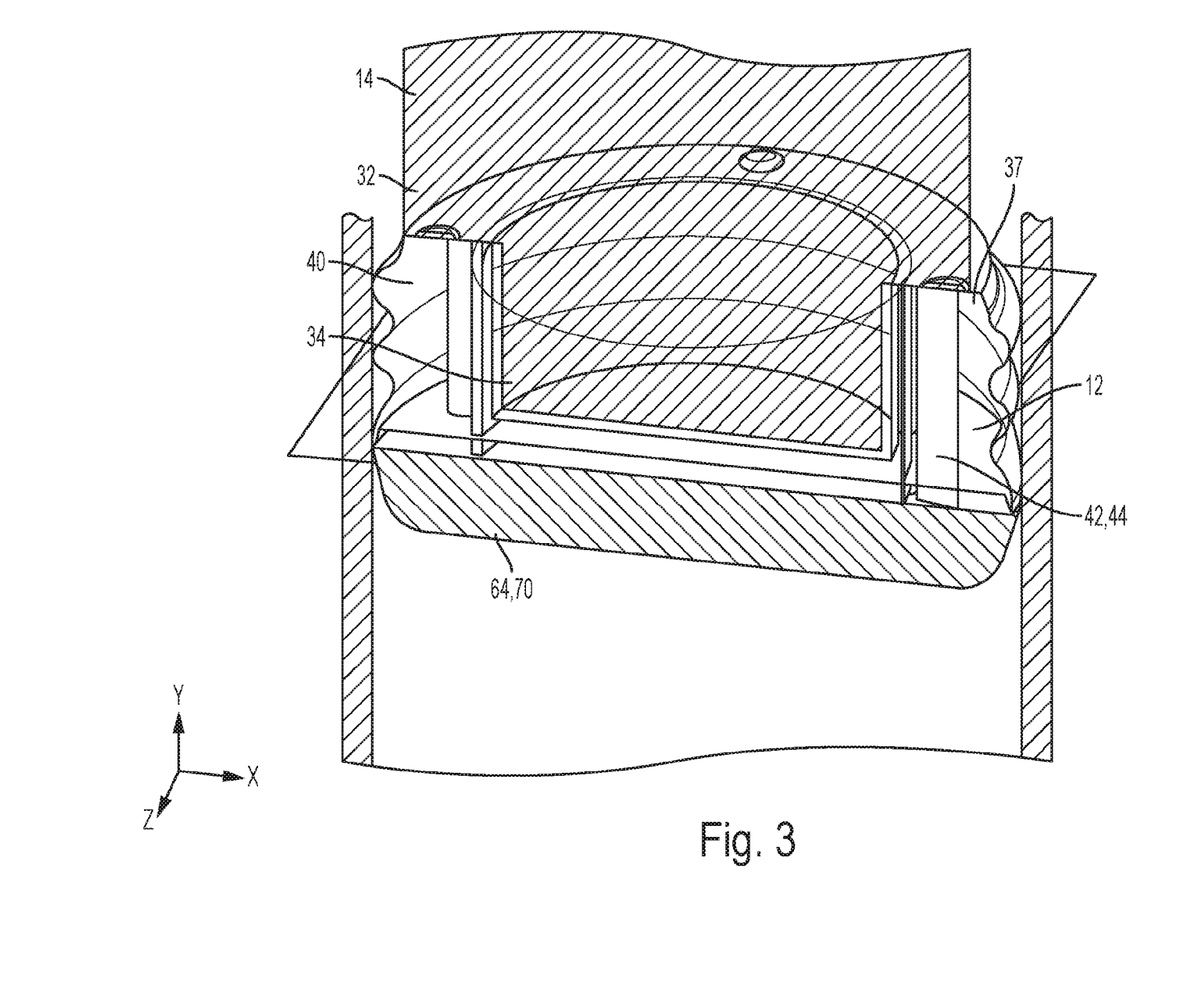
FIG. 3 is a cross-sectional view of the syringe assembly of FIG. 1 and the stopper of FIG. 2 in accordance with an embodiment of the invention.
Figure 4A:
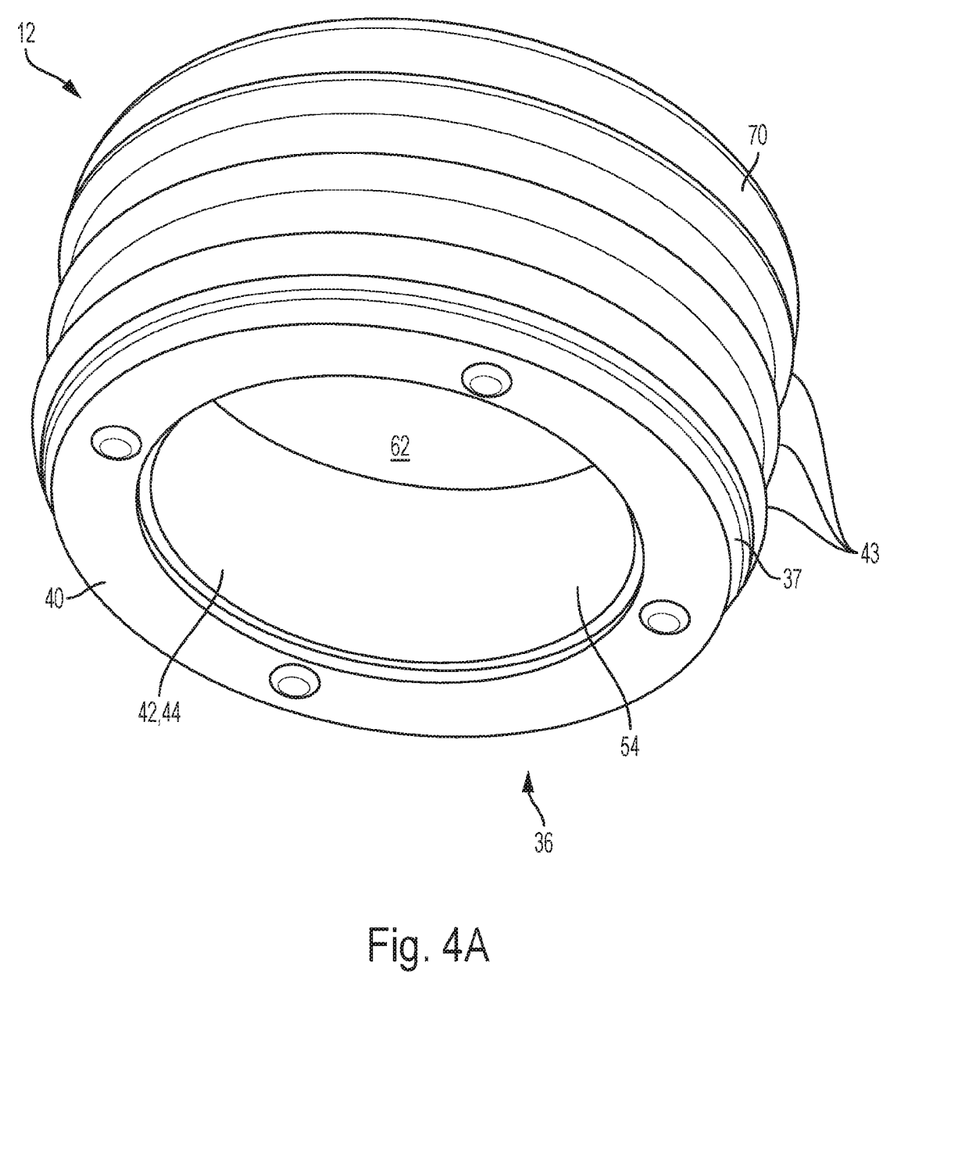
FIG. 4A is a bottom left perspective view of the stopper of FIG. 2 in accordance with an embodiment of the invention.

The plunger rod 14 includes an elongated body portion 26, a proximal end 28 having a flange 30 and a distal end 32. A base or connector portion 34 extends axially from the distal end 32 of the plunger rod 14 and has a diameter smaller than a diameter of the stopper 12, This connector portion 34 is configured to mate with a cavity 36 located at a proximal end 37 in the stopper 12 (as shown in FIGS. 3 and 4A). This mating engagement between the connector portion 34 and the stopper cavity 36 can be through a friction fit, a threaded engagement, or any other well-known arrangement. Typically, the connector portion 34 of the plunger rod 14 supports the stopper 12 at its center.

Reference is now made to FIGS. 2-4B which illustrate the stopper 12 in accordance with the invention. The stopper 12 comprises a first portion 40 formed from a first material and a second portion 42 formed from a second material. The stopper 12 includes a plurality of ribs 43 on its outside diameter. The first material of the first portion 40 of the stopper 12 may be made of any material suitable for providing sealing characteristics while under compression.

The second portion 42 formed from the second material has a greater rigidity than the first portion 40 formed from the first material. The second portion 42 is configured to be attached to the base or connector portion 34 of the plunger rod 14. According to one embodiment, the second portion 42 comprises an insert 44. The insert 44 can be formed from a semi-rigid or rigid material. According to one example, the insert 44 can be metal, such as aluminum, zinc, steel, or another other metals. According to another example, the insert 44 can be formed from a non-metallic material having rigid or semi-rigid properties, such as a high-temperature plastic or other materials known in the art. The insert 44 can be located within the cavity 36 of the stopper 12 and/or the stopper 12 can be molded about the insert 44 to form the cavity 36.

Figure 4B:
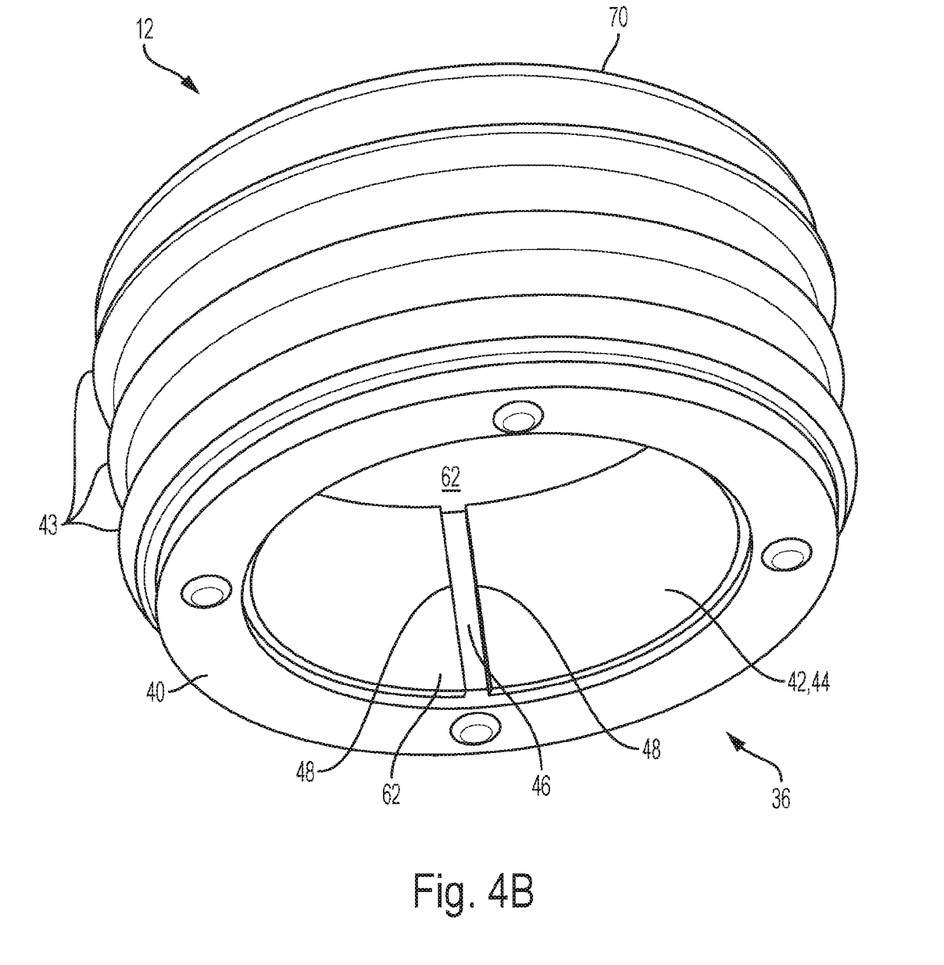
FIG. 4B is a bottom right perspective view of the stopper of FIG. 2 in accordance with an embodiment of the invention.
Figure 5:
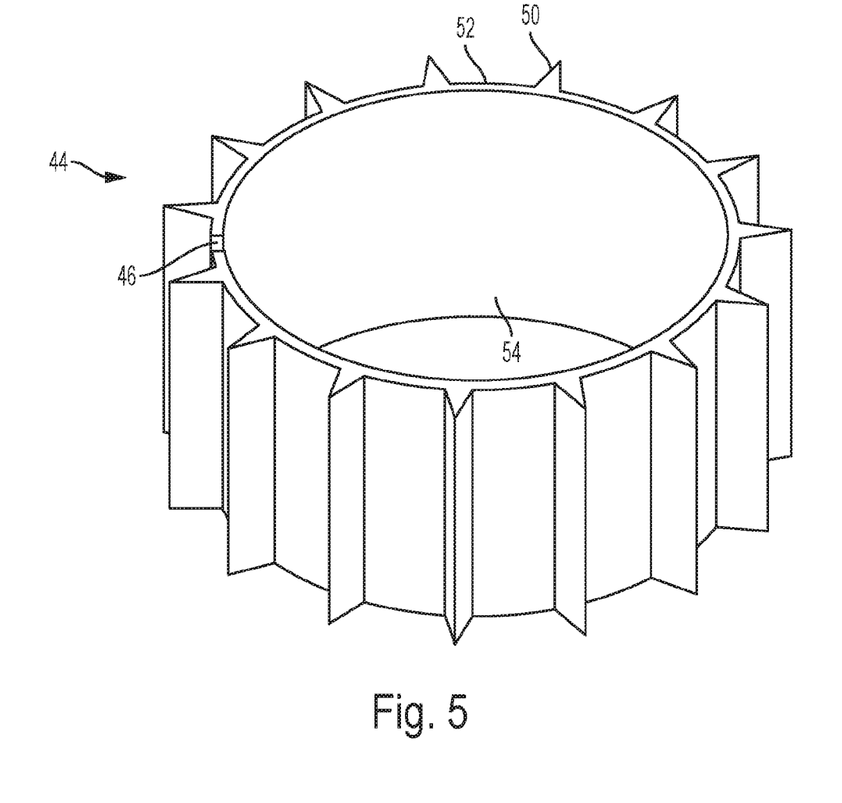
FIG. 5 is a top perspective view of the insert of the stopper of FIG. 2 in accordance with an embodiment of the invention.
Figure 6:
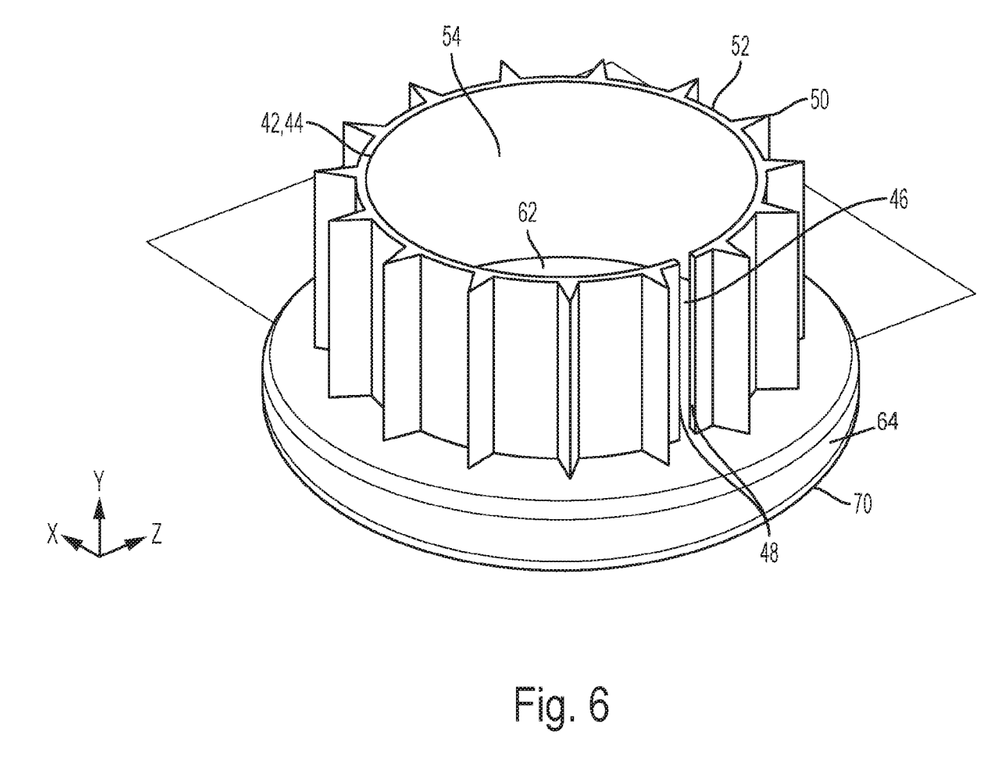
FIG. 6 is a bottom perspective view showing the insert and top portion of the stopper of FIG. 2 in accordance with an embodiment of the invention.
Figure 7:
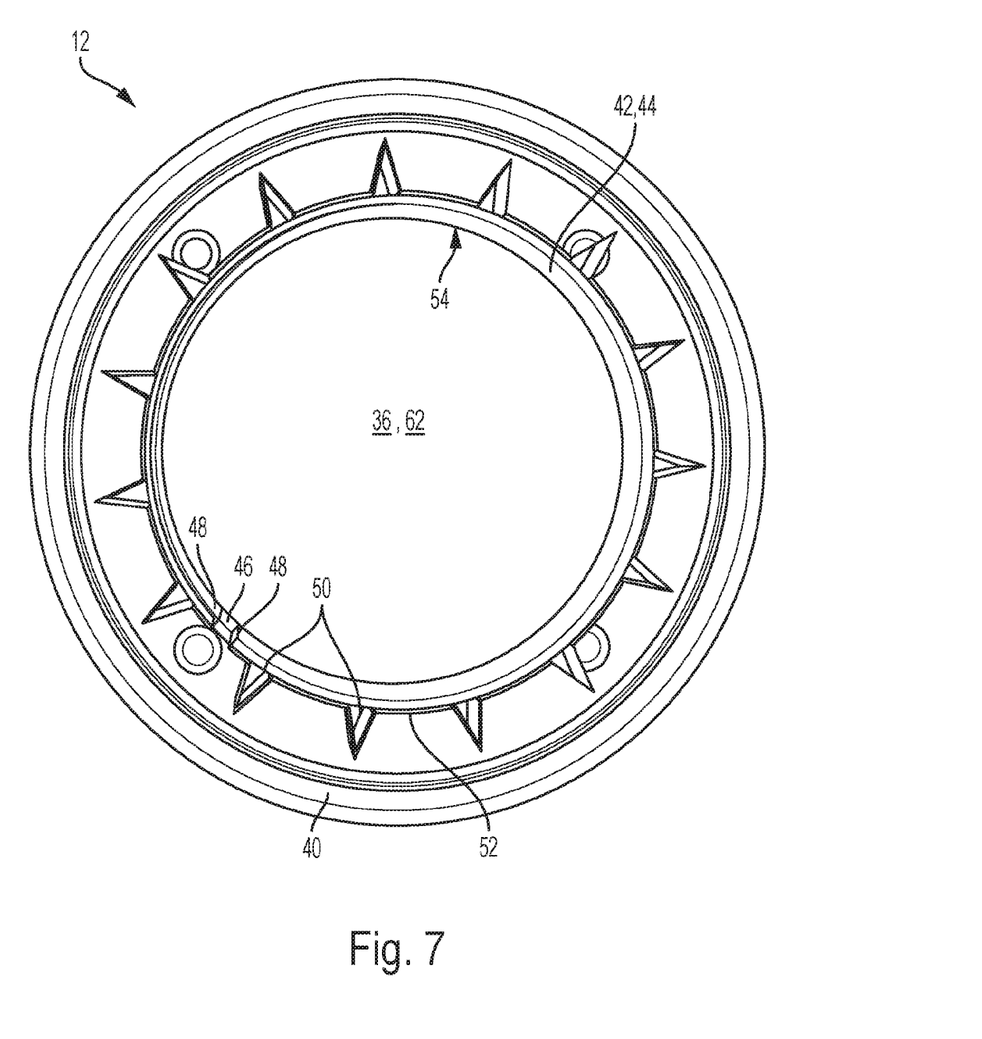
FIG. 7 is a bottom view of the stopper having the insert embedded therein of FIG. 2 in accordance with an embodiment of the invention.

With continuing reference to FIGS. 4A and 4B and with reference to FIGS. 5-7, the insert 44 can have a tubular shape. An open portion 46 can be formed between end portions 48 of the insert forming a "C"-shaped member, which provides some flexibility to the insert 44. As shown in FIGS. 5-7, according to one design, the insert 44 can have a plurality of radially extending barbs 50 that extend about an outer surface 52 thereof. These barbs 50 can be configured for embedding the second portion or insert 42, 44 within the first material of the first portion 40. Accordingly to one embodiment, the barbs 50 can have a triangular shape. The second portion or insert 42, 44 can have an inner surface 54 defining the cavity 36 of the stopper 12. This inner surface 54 can be smooth or can include internal threads (not shown) configured for mating with the base/connector portion 34 of the plunger rod 14.

The insert 44 can be formed by an injection molding or by an extrusion/cutting process or any other known process. Internal threads (not shown) can be formed within the insert 44 during the molding or extruding process for securing the stopper 12 to the plunger rod 14. It can be appreciated that the stopper 12 having the insert 44 can be secured to the plunger rod 14 by other well-known techniques, such as friction fit and the like.

The first material used to form the first portion 40 of the stopper 12 can comprise an elastomeric material, such as those materials typically used for stoppers, including, but not limited to any group of natural rubber, synthetic rubber, thermoplastic elastomers, or combinations thereof. The first material can be molded about the second portion/insert 42, 44. Alternatively, the insert 44 can be embedded in the first material of the first portion 40. In yet another design, the second portion/insert 44 can be fully encapsulated by the elastomeric material of the first portion 40 of the stopper 12. According to one embodiment and with particular reference to FIG. 6, the second portion/insert 44 can be first molded to an inner surface 62 of a front face 64 or "cap" located at the distal end of the stopper 12 and then a second mold shot of elastomeric material, forming the first portion 40, can fully encapsulate the insert 44. In this particular arrangement, the material of the first portion 40 will directly engage the connector portion 34 of the stopper 12. According to one embodiment, the insert 44 can have a closed front face (not shown) formed from the second material for abutting an inner surface 62 of the first material of the first portion, to directly support the front face 64 located at a distal end 66 of the stopper 12.

According to another embodiment, the stopper can comprise a third portion 70 forming the front face 64 of the stopper 12. This third portion 70 can be formed from a third material comprising an elastomeric material having barrier properties suitable for contacting the contents within the syringe barrel 16. According to one embodiment, the first portion 40 and third portion 70 can be formed from different materials and formed in a two-shot molding process. Alternatively, the first portion 40 and the third portion 70 can be formed from the same material and a barrier film can be separately laminated onto the front face 64 of the stopper. Suitable barrier films include, but are not limited to ethylene tetrafluoroethylene (ETFE), microporous membranes such as ePTFE, poplypropylene (PP) or polyethylene (PE), that minimize the drug product contact with the base rubber thereby blocking leeching of rubber components into the drug product.

Figure 8A:
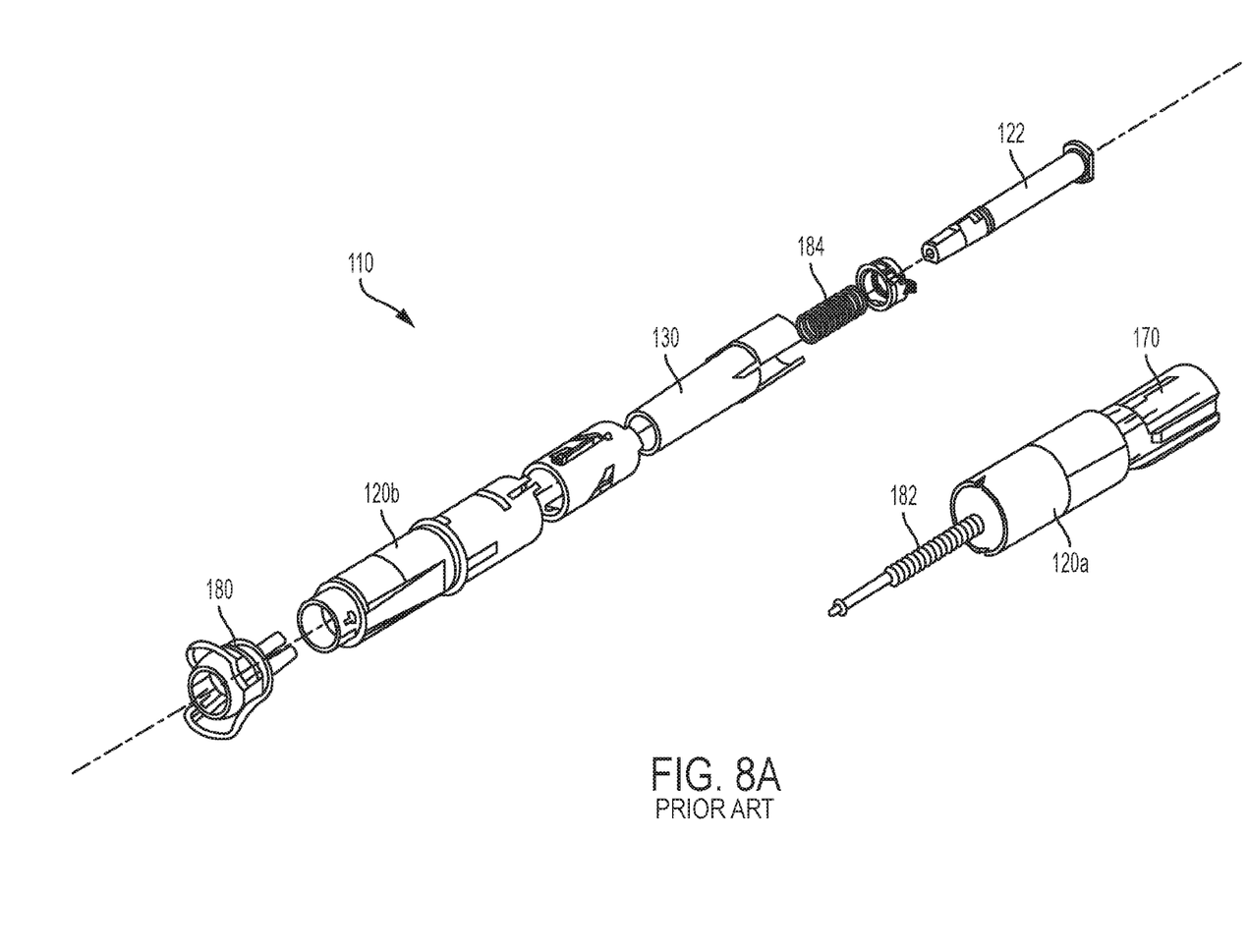
FIG. 8A is an exploded perspective view of an auto-injector in accordance with the prior art in which the stopper for high dose accuracy medication delivery of the invention can be utilized.
Figure 8B:
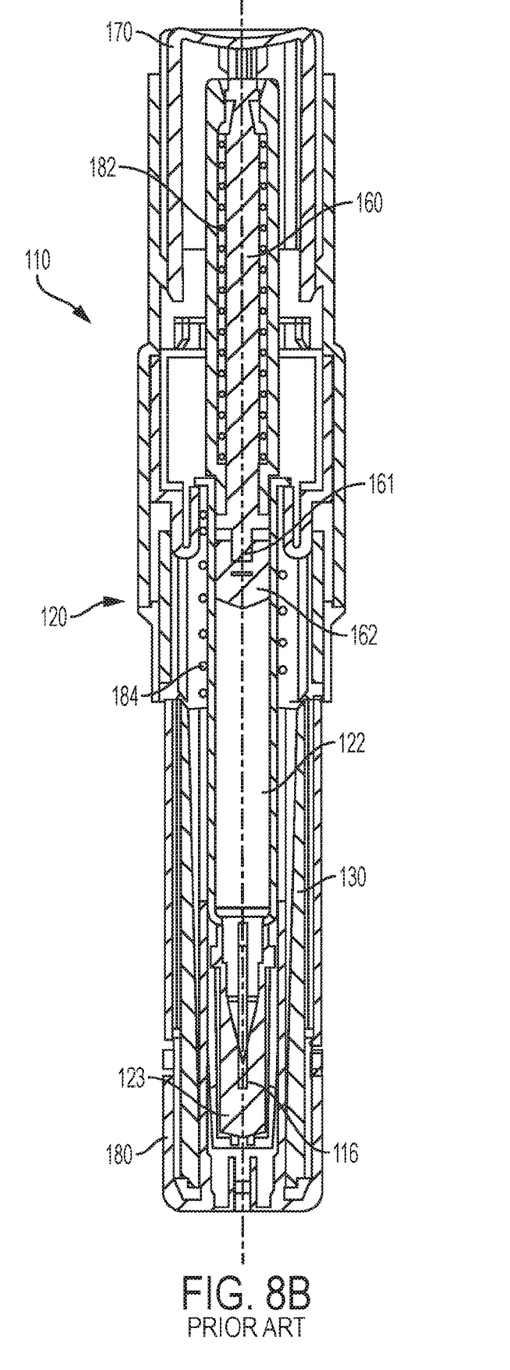
FIG. 8B is a cross-sectional view of the auto-injector of FIG. 8A in a ready to use position in accordance with the prior art in which the stopper for high dose accuracy medication delivery of the invention can be utilized.
Figure 8C:
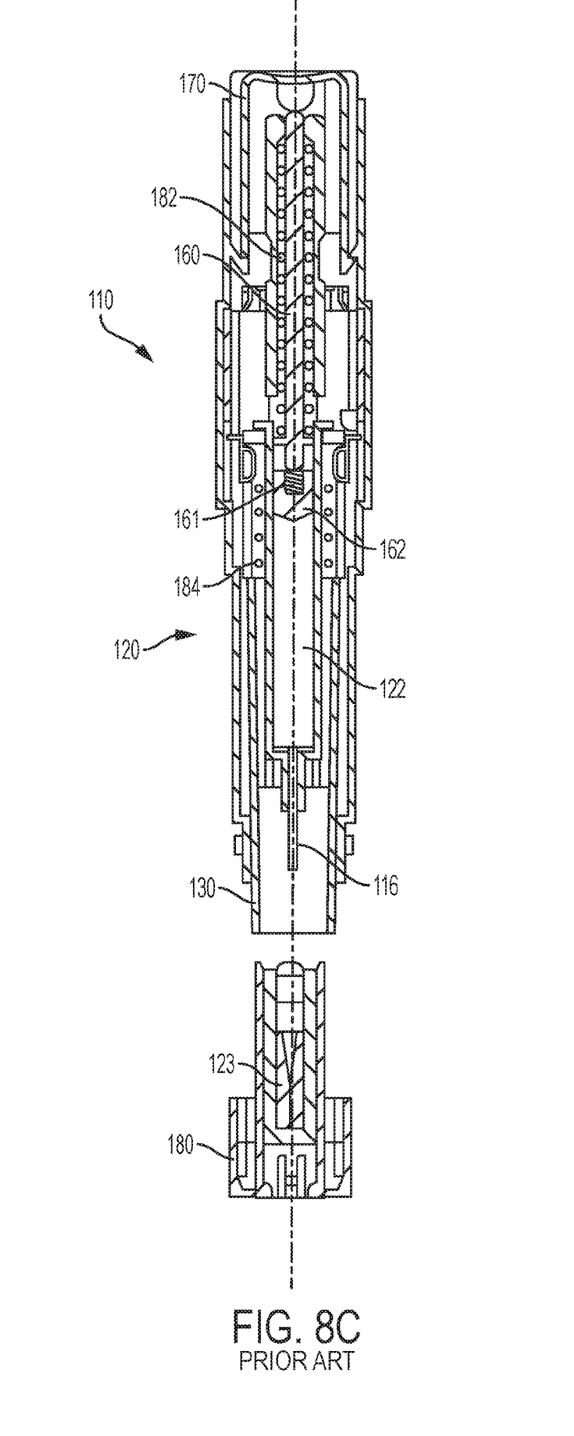
FIG. 8C is a cross-sectional view of the device of FIG. 8A after removal of the needle shield in accordance with the prior art in which the stopper for high dose accuracy medication delivery of the invention can be utilized.

Reference is now made to FIGS. 8A-8C, which show an example of an auto-injector, generally indicated as 110, in accordance with the prior art in which the stopper for high dose accuracy drug delivery of the invention can be utilized. The auto-injector 110 includes a housing, indicated as 120a and 120 in FIG. 8A and generally indicated as 120 in FIGS. 8B and 8C, enclosing a container 122 having fluid or medicament located therein. The container 122 has an open proximal end and a substantially closed distal end having a needle 116 associated therewith. The container 122 is movable relative to the housing 120. A stopper 162 located within the container 122 and is associated with a distal end portion 161 of a piston rod 160. The piston rod 160 can be a spring-loaded piston rod via spring 182. A push button 170 can be provided to act as a trigger for the auto-injector 110. The device also includes a spring 184 between a container 122 and a safety shield 130. Upon removal of a deshielder 180 and needle shield 123, the device is ready for activation. The user then applies the distal end of the safety shield 130 on the site of injection and applies a distal force on the housing 120, which causes the safety shield 130 to move in a proximal direction and compress the spring 184 and place the container 122 in an active state. The injection step can now be triggered by the application of a distally directed pushing force to the push button 170.

In accordance with the present invention, the stopper 162, shown in FIGS. 8B and 8C can be replaced with the stopper 12 of the present invention, as shown in FIGS. 2-4B and discussed in detail above. The replacement of stopper 162 with the high dose accuracy stopper 12 of the present invention will increase the accuracy of the fluid or medicament being dispensed by the auto-injector. As discussed above, the stopper 12 includes a first portion 40 formed from a first material and a second portion 42 formed from a second material. The first material of the first portion 40 of the stopper 12 may be made of any material suitable for providing sealing characteristics while under compression. The second portion 42 formed from the second material has a greater rigidity than the first portion 40 formed from the first material. The second portion 42 can be attached to the distal end portion 161 of the piston rod 160 of FIGS. 8B and 8C. The second portion 42 can comprises an insert 44 formed from a semi-rigid or rigid material. The insert 44 can be located within the cavity 36 of the stopper 12 and/or the stopper 12 can be molded about the insert 44 to form the cavity 36. The auto-injector can then be operated in the same manner as the auto-injector of FIGS. 8A-8C. Use of the stopper 12 of the invention can improve the dose accuracy of the drug due to its reduced amount of distortion during advancement, its lower contact pressure in a resting state, and it reduced amount of hysteresis.

Figure 9A:
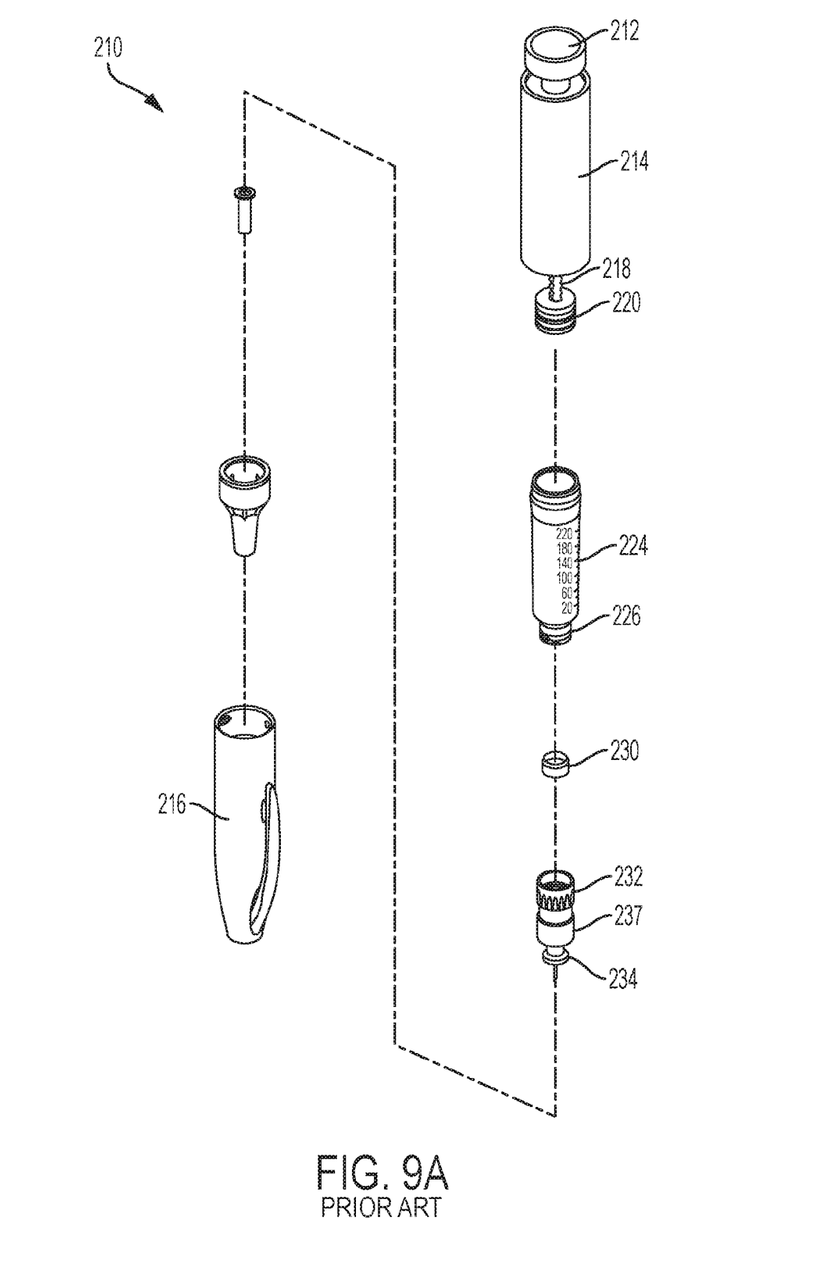
FIG. 9A is an exploded perspective view of the components of a medication delivery pen injection device in accordance with the prior art in which the stopper for high dose accuracy medication delivery of the invention can be utilized.
Figure 9B:
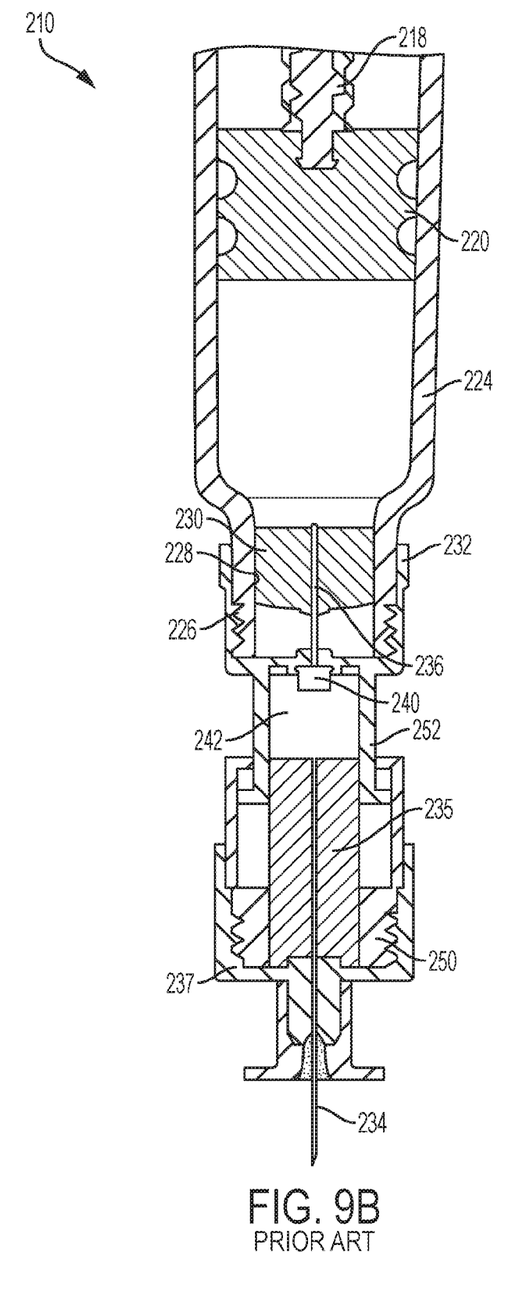
FIG. 9B is a partial cross-sectional view of the medication delivery pen injection device in a dosed and loaded state in accordance with the prior art in which the stopper for high dose accuracy medication delivery of the invention can be utilized.

Reference is now made to FIGS. 9A and 9B, which show an injection medication delivery pen generally indicated as 210, in accordance with the prior art in which the stopper for high dose accuracy drug delivery of the invention can be utilized. The injection pen injection device 210 comprises a dose knob/button 212, an outer sleeve 214, and a cap 216. The dose knob/button 212 allows a user to set the dosage of medication to be injected. The outer sleeve 214 is gripped by the user when injecting medication. The cap 216 is employed by the user to securely hold the pen injector 210 in a shirt pocket, purse, or other suitable location. The dose knob/button 212 has a dual purpose and is used to both set the dosage of the medication to be injected and to inject the dosed medicament via a lead screw 218 and stopper 220 from a medicament cartridge 224, which is attached to the medication delivery pen through a reservoir housing 232. The medicament cartridge 224 is typically attached to a standard pen injector housing via known attachment means. The medicament cartridge 224 can comprise a tube sealed at end 228 with a septum 230 and at the other end with the stopper 220. In standard drug delivery pens, the dosing and delivery mechanisms are all found within the outer sleeve 214. Those mechanisms are not described in greater detail herein as they are understood by those knowledgeable of the art. The pen needle assembly 210 includes a patient needle 234 held by a sliding seal 235 and extending from a pen needle assembly 237 at a patient end and a septum-penetrating needle cannula 236 disposed within the housing reservoir 232 on a non-patient side thereof. The septum-penetrating needle cannula 236 is in fluid communication with the patient needle 234 via check valve 240 and secondary reservoir 242. The pen needle assembly 237 can be associated with the reservoir housing 232 via a pen needle connecting portion 250 and a wall portion 252 of the secondary reservoir 242 by a threaded arrangement, such as threads on the reservoir housing 232, although other attachment means can be used, such as attaching directly to the medicament cartridge 224 via threads 226. Upon attachment of the reservoir housing 232 to the medicament cartridge 224, the septum-penetrating cannula 236 pierces the septum 230, but the septum 230 does not move with respect to the medicament cartridge 224. The stopper 220, however, is axially displaceable within the medicament cartridge 224 while maintaining a fluid-tight seal. The distal movement of the stopper 220 within the medicament cartridge 224 (due to advancement of the lead screw 218) causes medication to be forced into the patient needle 234 of the needle assembly 237.

In accordance with the invention, the stopper 220 of the injection pen 210 can be replaced with the stopper 12 of the present invention, as shown in FIGS. 2-4B and discussed in detail above. The stopper 12 can be secured onto the lead screw 218, shown in FIGS. 9A and 9B. As discussed above, the stopper 12 includes a first portion 40 formed from a first material and a second portion 42 formed from a second material. The first material of the first portion 40 of the stopper 12 may be made of any material suitable for providing sealing characteristics while under compression. The second portion 42 formed from the second material has a greater rigidity than the first portion 40 formed from the first material. The second portion 42 can be attached to the lead screw 218 of the plunger rod 14. The second portion 42 can comprises an insert 44 formed from a semi-rigid or rigid material. The insert 44 can be located within the cavity 36 of the stopper 12 and/or the stopper 12 can be molded about the insert 44 to form the cavity 36. The dose knob/button 212 can be used to set the dosage of the medication to be injected and to inject the dosed medicament via the lead screw 218 and stopper 12 of the invention, from the medicament cartridge 224. Use of the stopper 12 of the invention can improve the dose accuracy of the drug due to its reduced amount of distortion during advancement, its lower contact pressure in a resting state, and it reduced amount of hysteresis.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure that is known or customary practice in the art to which this disclosure pertains and which fall within the limits of the appended claims.

The invention claimed is:

1. A stopper adapted for attachment with a plunger rod for use within a syringe barrel for accurate dispensing of a fluid, the stopper comprising a first portion formed from a first material and a second portion formed from a second material, wherein the second material has a greater rigidity than the first material and wherein the second portion is configured to be attached to the plunger rod;
   wherein the first portion comprises a cavity;
   wherein the second portion comprises a tubular member having opposing open top and bottom ends, the tubular member positioned within the cavity of the first portion; and
   wherein the tubular member comprises a C-shaped tubular member having an open portion that provides flexibility to the second portion for placement and retention within the cavity.

2. The stopper of claim 1, wherein the second portion comprises an insert.

3. The stopper of claim 2, wherein the insert is formed from metal.

4. The stopper of claim 2, wherein the insert is formed from a non-metallic material.

5. The stopper of claim 4, wherein the insert is formed by an injection molding or by an extrusion and cutting process.

6. The stopper of claim 2, wherein the insert is embedded in the first material of the first portion.

7. The stopper of claim 1, wherein the second portion includes internal threads for mating with the plunger rod.

8. The stopper of claim 1, wherein the first material comprises an elastomeric material.

9. The stopper of claim 1, wherein the first material is molded about the second material.

10. The stopper of claim 1, wherein the tubular member has radially extending barbs about an outer surface thereof configured for embedding the second portion within the first material of the first portion.

11. The stopper of claim 1, wherein the stopper comprises a third portion forming a distal end of the stopper, the third portion formed from a third material comprising an elastomeric material having barrier properties or coated with a barrier film.

12. A stopper adapted for attachment with a piston rod for use with an auto-injector for accurate dispensing of a fluid, the stopper comprising a first portion formed from a first material and a second portion formed from a second material, wherein the second material has a greater rigidity than the first material, and wherein the second portion is configured to be attached to a spring-loaded piston rod;
   wherein the first portion comprises a cavity;
   wherein the second portion comprises a tubular member having opposing open top and bottom ends, the tubular member positioned within the cavity of the first portion; and
   wherein the tubular member comprises a C-shaped tubular member having an open portion that provides flexibility to the second portion for placement and retention within the cavity.

13. The stopper of claim 12, wherein the first material comprises an elastomeric material and the second portion comprises an insert formed from metal or a high-temperature plastic and wherein the insert is embedded within the elastomeric material of the first portion.

14. A stopper adapted for attachment with a lead screw for use with an injection pen having a dosage knob for accurate dispensing of a fluid, the stopper comprising a first portion formed from a first material and a second portion formed from a second material, wherein the second material has a greater rigidity than the first material, and wherein the second portion is configured to be attached to the lead screw;
- wherein the first portion comprises a cavity;
- wherein the second portion comprises a tubular member having opposing open top and bottom ends, the tubular member positioned within the cavity of the first portion; and
- wherein the tubular member comprises a C-shaped tubular member having an open portion that provides flexibility to the second portion for placement and retention within the cavity.

15. The stopper of claim 14, wherein the dosage knob and lead screw set the dosage of the fluid to be injected and to inject the dosed fluid via the lead screw and the stopper from a medicament cartridge attached to a medication delivery pen.

16. The stopper of claim 14, wherein the first material of the first portion comprises an elastomeric material and the second portion comprises an insert formed from metal or a high-temperature plastic and wherein the insert is embedded within the elastomeric material of the first portion.

* * * * *